(12) United States Patent
Denker et al.

(10) Patent No.: US 7,532,932 B2
(45) Date of Patent: May 12, 2009

(54) IMPLANTABLE MEDICAL APPARATUS HAVING AN OMNIDIRECTIONAL ANTENNA FOR RECEIVING RADIO FREQUENCY SIGNALS

(75) Inventors: Stephen Denker, Mequon, WI (US); Arthur J. Beutler, Greendale, WI (US)

(73) Assignee: Kenergy, Inc., Mequon, WI (US)

( * ) Notice: Subject to any disclaimer, the term of this patent is extended or adjusted under 35 U.S.C. 154(b) by 679 days.

(21) Appl. No.: 11/075,412

(22) Filed: Mar. 8, 2005

(65) Prior Publication Data

US 2006/0206170 A1    Sep. 14, 2006

(51) Int. Cl.
*A61N 1/00* (2006.01)
(52) U.S. Cl. .............................. 607/32; 607/60; 128/903
(58) Field of Classification Search ........................ None
See application file for complete search history.

(56) References Cited

U.S. PATENT DOCUMENTS

| 4,044,775 | A | * | 8/1977 | McNichols | .................... 607/61 |
| 4,441,498 | A | * | 4/1984 | Nordling | ..................... 607/32 |
| 5,411,535 | A | | 5/1995 | Fujii et al. | |
| 5,531,779 | A | | 7/1996 | Dahl et al. | |
| 6,009,350 | A | * | 12/1999 | Renken | ......................... 607/32 |
| 6,058,330 | A | | 5/2000 | Borza | |
| 6,111,520 | A | | 8/2000 | Allen et al. | |
| 6,201,387 | B1 | | 3/2001 | Govari | |
| 6,278,379 | B1 | | 8/2001 | Allen et al. | |
| 6,445,953 | B1 | | 9/2002 | Bulkes et al. | |
| 2003/0229647 | A1 | * | 12/2003 | Mejia et al. | ............... 707/104.1 |
| 2004/0088012 | A1 | * | 5/2004 | Kroll et al. | ..................... 607/9 |
| 2004/0171355 | A1 | * | 9/2004 | Yu et al. | ......................... 455/78 |
| 2005/0107847 | A1 | | 5/2005 | Gruber et al. | |

FOREIGN PATENT DOCUMENTS

| EP | 0 989 382 | | 3/2000 |
| EP | 989384 | A2 * | 3/2000 |

* cited by examiner

*Primary Examiner*—Carl H. Layno
*Assistant Examiner*—Jon-Eric C. Morales
(74) *Attorney, Agent, or Firm*—Quarles & Brady LLP; George E. Haas

(57) ABSTRACT

An radio frequency antenna assembly is provided for a medical device such as one capable of being implanted into a patient. The antenna assembly includes a plurality of antennas, each oriented to receive a radio frequency signal propagating along a different axis. This facilitates reception of the radio frequency signal regardless of the orientation of its propagation axis to the medical device. In other cases, the radio frequency signal has a plurality of components, each propagating along a different axis, and each antenna of the assembly receives a different one of those components. The individual electrical signals produced in each antenna are additively combined into a single signal having greater strength than each of the individual electrical signals.

20 Claims, 2 Drawing Sheets

IMPLANTABLE MEDICAL APPARATUS HAVING AN OMNIDIRECTIONAL ANTENNA FOR RECEIVING RADIO FREQUENCY SIGNALS

CROSS-REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

1. Field of the Invention

The present invention relates to medical devices for implanting into an animal, such as cardiac stimulation devices, and more particularly to such medical devices that receive radio frequency signals via an antenna.

2. Description of the Related Art

A remedy for people with slowed or disrupted natural heart beats is to implant a cardiac pacing device which is a small electronic apparatus that stimulates the heart to beat at regular intervals. That device consists of a pulse generator, implanted in the patient's chest, which produces electrical pulses that stimulate heart contractions. Electrical wires extend from the pulse generator to several electrodes placed nearby specific muscles of the heart, which when electrically stimulated produce contraction of the adjacent heart chambers.

It is quite common that the wires extend through arteries or veins which enter the heart so that the electrodes can be placed in the muscle of the heart chamber requiring stimulation. The wires typically extend for some distance in the arteries or veins and may pass through one or two heart valves. In other patients, patch electrodes are placed on the exterior heart surface with wires extending through tissue to the pacing device. With either type of wire placement, it is important that the electrodes be attached at proper positions on the heart to stimulate the muscles and produce contractions. Thus, it is desirable to properly locate the electrodes for maximum heart stimulation with minimal adverse impact to other physiological functions, such as blood circulation.

More recently wireless pacing devices have been proposed, such as the one described in U.S. Pat. No. 6,445,953. With this type of device, a radio frequency (RF) signal is transmitted from a conventional pacing circuit to stimulator devices placed on the heart at locations where stimulation is to occur. For example, the stimulator device can be implanted in a blood vessel of the heart. The radio frequency signal activates the device which applies an electrical pulse to the heart tissue. Electrical power for stimulating the heart is derived from the energy of the radio frequency signal.

One of the difficulties in such a wireless system is ensuring that the radio frequency signal and a maximum amount of the RF energy is received by the stimulator device. In the case of that prior patented device, the antenna was a coil wrapped around a cylindrical structure that was embedded against the wall of a vein or artery. That type of antenna received the greatest amount of energy from an electromagnetic field oriented in a direction through the turns of the coil. However, since the antenna can be implanted in different orientations in the patient's body depending on the location of the vein or artery and the orientation of the transmitter antenna similarly varies, it is difficult to ensure that the electromagnetic field from the RF signal will be properly aligned with the antenna of the implanted device. Because choosing the location at which the medical device in implanted is based primarily on cardiac stimulation criteria, it is not always possible to optimally orient its antenna for maximum energy reception.

A proposed transmitter, for sending signals to the implanted medical device, employs an omnidirectional antenna which emits electromagnetic waves that propagate along three orthogonal axes. Thus one of those electromagnetic waves or a vector sum of two or all of them will be aligned with the antenna coil of the implanted medical device. Although this solves the problem of misalignment of the transmitter and receiver antennas, the RF energy from all the electromagnetic waves is not received by the implanted device. Since that device is powered by the RF energy, it is desirable to receive as much of the transmitted energy as possible. That desire is especially acute when the medical device is an implanted defibrillator as such apparatus requires a relatively large amount of power to defibrillate a heart.

SUMMARY OF THE INVENTION

An antenna assembly is provided by which an medical device, such as one implanted in a patient, receives a radio frequency signal. The assembly has a first antenna oriented on the medical device to receive a component of the radio frequency signal that propagates along a first axis. A second antenna is oriented on the medical device to receive a component of the radio frequency signal that propagates along a second axis that is transverse to the first axis.

In one version of the antenna assembly the first and second antennas are oriented along separate orthogonal axes. Preferably, each of the first and second antennas comprises two conductive coils that are electrically connected together and spaced apart along the respective axis. The preferred embodiment of the antenna assembly further includes a third antenna oriented along a third axis that is orthogonal to both the first and second axes.

Another aspect of the present antenna assembly provides a circuit that is operably connected to combine electrical signals produced in all the antennas.

The present antenna assembly is particularly adapted for use with an implanted medical device that has a cylindrical body. Here, a first antenna is oriented on the cylindrical body to receive the radio frequency signal and a second antenna is oriented on the cylindrical body at a location that is spaced 90° circumferentially from the first antenna. Each of the first and second antennas may comprise two coils located on opposite sides of the body and interconnected so that electrical signal produced in the two coils additively combine. In this medical device, a third antenna may be wound circumferentially around the body.

The various versions of the present antenna assembly provide multiple antennas each for receiving the radio frequency signal that propagates along a given axis. This enhances reception of the radio frequency signal regardless of the orientation of the medical device to the propagation axis. In other cases, the radio frequency signal has a plurality of components, each propagating along a different axis and each antenna of the assembly receives a different one of those component. The individual electrical signals produced in each antenna are additively combined into a single signal having greater strength than each of the individual electrical signals.

DETAILED DESCRIPTION OF THE INVENTION

Figure 1:
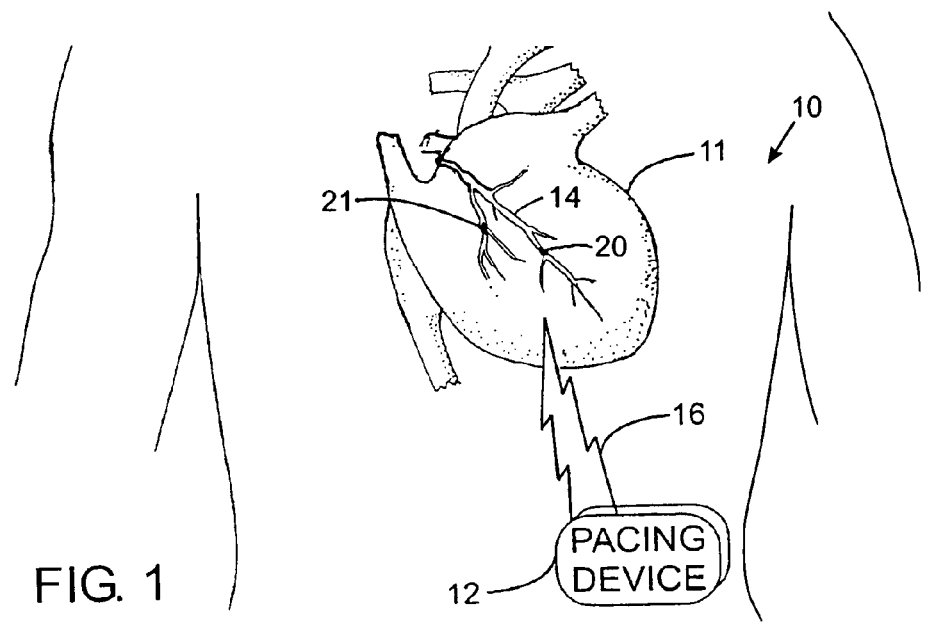
FIG. 1 depicts a cardiac pacing apparatus implanted in a patient.

With initial reference to FIG. 1, an apparatus 10 for applying electrical stimulation to a heart 11 comprises a pacing device 12 and one or more stimulators 20 and 21 located in arteries or veins 14 through which blood flows within the heart muscles. As will be described in greater detail, the pacing device 12 emits a radio frequency signal 16 which produces an electric current in the implanted vascular stimulators, thereby stimulating the heart muscle to contract. The radio frequency signal 16 preferably comprises a set of electromagnetic waves the propagate along three orthogonal axes, however that signal alternatively may comprise a single electromagnetic wave or other pluralities of waves. Although the present invention is being described in the context of an apparatus for pacing the heart, the novel antenna system can be used with defibrillators and other implantable medical devices.

Figure 2:
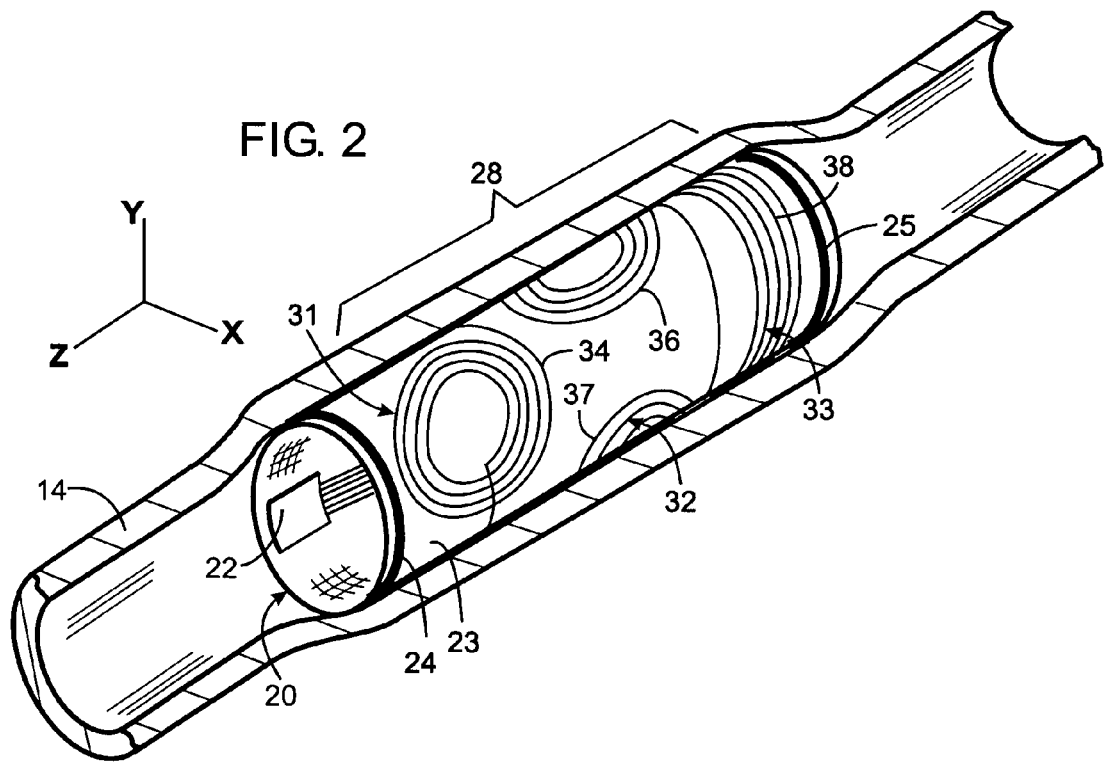
FIG. 2 is an isometric, cut-away view of a blood vessel with a cardiac stimulation device implanted therein.

Referring to FIG. 2, a stimulator 20 is placed in the artery or vein 14 of the heart 11. The body 23 of the stimulator 20 has a design similar to well-known vascular stents and is in the form of a tube that initially is collapsed to a relatively small diameter enabling it to pass freely through arteries or veins of a patient. The procedure for implanting the stimulator 20 is similar to that used for vascular stents. For example, the balloon at the end of a standard catheter is inserted into the annulus of the stimulator 20 in the collapsed, or reduced diameter, configuration. That assembly is inserted through an incision in a vein or artery near the skin of a patient and threaded through the vascular system to the appropriate location in the heart. Specifically, the stimulator 20 ultimately is positioned in a cardiac artery or vein 14 adjacent to a section of the heart muscle where stimulation should be applied. The balloon of the catheter then is inflated to expand the vascular stimulator 20 which, as seen in FIG. 2, embeds the stimulator against the wall of the blood vessel. The balloon is deflated, the catheter is removed from the patient, and the incision is closed. Thereafter, the tubular configuration of the stimulator allows blood to flow relatively unimpeded through the artery or vein.

Figure 3:
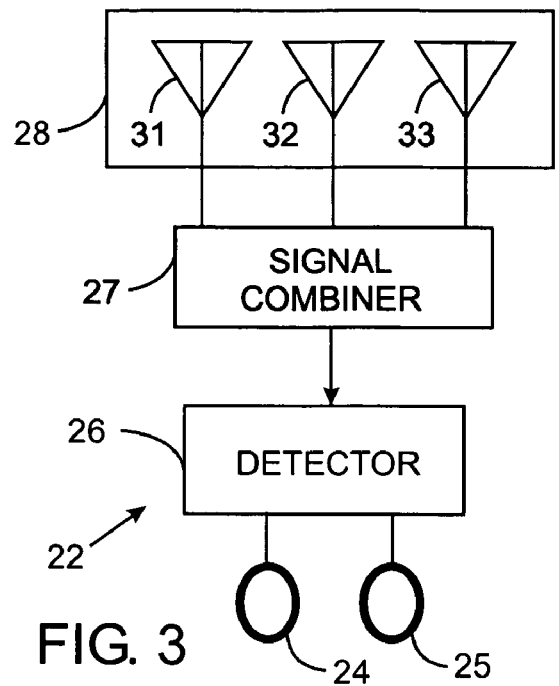
FIG. 3 is a schematic block diagram of an electrical circuit on the stimulation device.

With reference to FIGS. 2 and 3, a signal receiving circuit 22 is mounted on the body 23 of the vascular stimulator 20. The signal receiving circuit 22 includes an antenna array 28, a passive RF signal combiner 27, a radio frequency signal detector 26, and first and second electrodes 24 and 25. The antenna array 28 preferably comprises three antennas 31, 32 and 33 connected by a signal combiner 27 to inputs of the radio frequency signal detector 26 that is tuned to the frequency (e.g. 27 MHz.) of the RF signal 16 emitted by the pacing device 12. However, the detector does not necessarily have to be a tuned circuit. Upon receiving the radio frequency signal 16, the detector 26 converts the energy of that signal into a differential voltage pulse that is applied across the first and second electrodes 24 and 25. Those electrodes form an electric circuit path with the patient's heart tissue, thereby stimulating that tissue. Thus, each time the pacing device 12 emits a radio frequency signal 16, a pulse of electrical voltage is produced in the vicinity of the stimulator 20 to stimulate the adjacent heart muscle.

The three separate antennas 31, 32 and 33 of the antenna array 28 are oriented on the body 23 to receive radio frequency electromagnetic waves that propagate along three orthogonal axes designated X, Y and Z, respectively. The first antenna 31 includes first and second coils 34 and 35 mounted on opposite lateral sides of the exterior surface of the body 23 (only one of those coils 34 is visible in FIG. 2, but see FIG. 4). The first antenna 31 receives electromagnetic waves, or components of such waves, that propagate in the X axis. The second antenna 32 is formed by third and fourth coils 36 and 37 mounted on the top and bottom of the exterior surface of the body 23 and receives electromagnetic waves, or components of such waves, that propagate in the Y axis. It should be understood that the directional references herein to lateral sides, top, and bottom are for understanding the physical relationship between the first and second antennas 31 and 32 and relates only to the orientation of the stimulator body 23 in FIG. 2, which orientation may be rotated in a particular installation of the stimulator in a patient. The third antenna 33 is a single fifth coil 38 that is wound circumferentially around the exterior surface of the body 23 to receive electromagnetic waves, or components of such waves, that propagate in the Z axis. The ends of the fifth coil 38 are connected to the RF signal combiner 27 which is a passive network that combines the signals from the three antennas 31-33 into a single signal that is fed to the detector 26.

Figure 4:
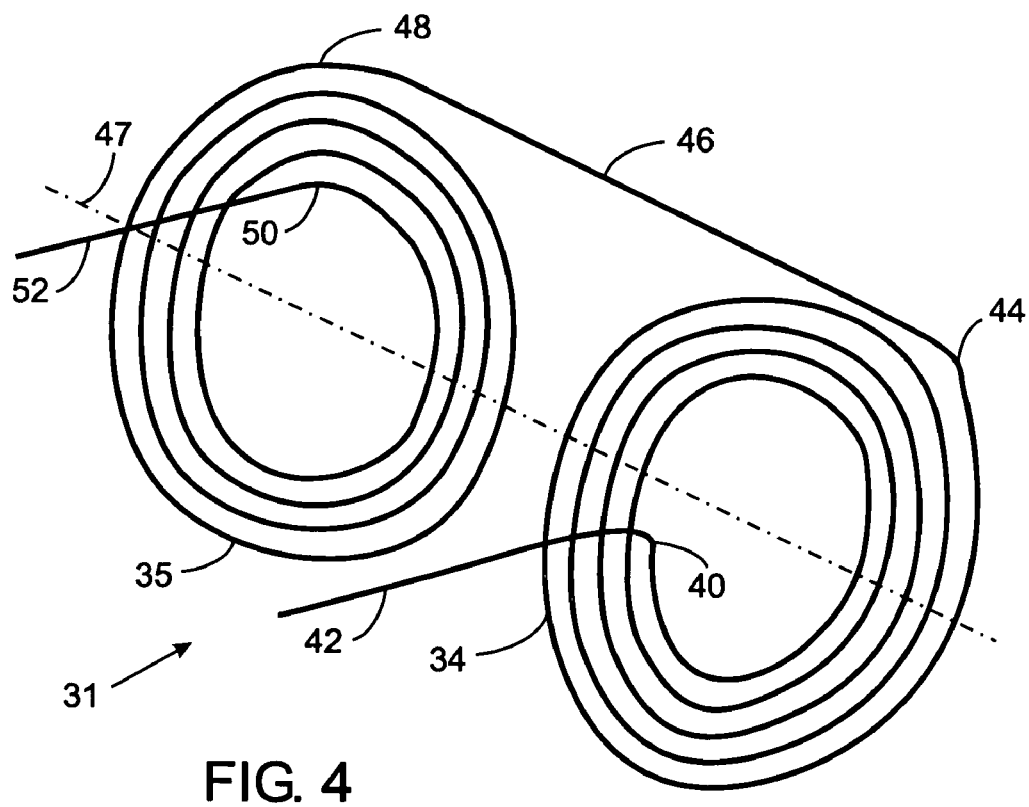
FIG. 4 depicts one of the antennas of the stimulation device.

The interconnection of the first and second coils 34 and 35 of the first antenna 31 is depicted in FIG. 4. It should be understood that the third and fourth coils 36 and 37 of the second antenna 32 have the same construction as coils first and second 34 and 35, respectively, with the only distinction being rotation 90° around the circumference of the body 23. The first coil 34 has a first end 40 connected by a conductor 42 to the signal combiner 27 of the signal receiving circuit 22. The first coil 34 is wound counter clockwise in an increasing radius spiral until reaching a second end 44. The number of turns of the spiral is chosen to optimum reception of the particular frequency of the RF signal from the pacing device 12. The second end 44 of the first coil 34 is connected by a linking conductor 46 to a first end 48 of the second coil 35.

The second coil 35 centered diametrically opposite the center of the first coil 34 along axis 47 and is wound from its first end 48 in a clockwise decreasing radius spiral until reaching a second end 50. The second coil 35 preferably has the same number of turns as the first coil 34. The second end 50 of the second coil 35 is connected by another conductor 46 to the signal combiner 27. It should be understood that the spirals of the first and second coils 34 and 35 may be wound in the opposite direction that those shown in FIG. 4. However, electric current induced in the first antenna by the RF signal from the pacing device 12 must flow in the same direction, clockwise or counter clockwise in both coils. In other words, the two coils 34 and 35 are wound so that the electric current induced in each one combine in an additive manner to produce a resultant current that is greater than the current induced in either coil alone.

The foregoing description was primarily directed to a preferred embodiment of the invention. Although some attention was given to various alternatives within the scope of the invention, it is anticipated that one skilled in the art will likely realize additional alternatives that are now apparent from disclosure of embodiments of the invention. Accordingly, the scope of the invention should be determined from the following claims and not limited by the above disclosure.

What is claimed is:

1. An antenna assembly by which a medical device receives a radio frequency signal that has a B field, said antenna assembly comprising:
    a body having a cylindrical surface;
    a first antenna located on the cylindrical surface to receive a B field that is oriented in a first direction, the first antenna comprising a first conductive coil and a second conductive coil connected in series and spaced along a first axis; and
    a second antenna located on the cylindrical surface to receive to receive a B field that is oriented in a second direction that is transverse to the first direction, the second antenna comprises a third conductive coil and a fourth conductive coil connected in series and spaced along a second axis that is transverse to the first axis.

2. The antenna assembly as recited in claim 1 wherein the second direction is orthogonal to the first direction.

3. The antenna assembly as recited in claim 1 wherein the first antenna and the second antenna each comprises a conductive coil wherein the conductive coil of the first antenna is orthogonal to the conductive coil of the second antenna.

4. The antenna assembly as recited in claim 1 further comprising a third antenna oriented at the medical device to receive a B field that is oriented in a third direction that is transverse to the first direction and the second direction.

5. The antenna assembly as recited in claim 4 wherein the first antenna, the second antenna, and the third antenna each comprises a conductive coil wherein the conductive coil of each antenna is orthogonal to the conductive coil of the other antennas.

6. The antenna assembly as recited in claim 1 further comprising a third antenna that has a fifth conductive coil wound about a third axis that is transverse to the first axis and the second axis.

7. The antenna assembly as recited in claim 1 further comprising a passive network connected to the first antenna and the second antenna and combining electrical signals produced in those antennas.

8. The antenna assembly as recited in claim 1 wherein the medical device has a body to which the first antenna and the second antenna are mounted, and wherein the first conductive coil and the second conductive coil are mounted on opposite sides of the body and the second conductive coil are mounted on opposite sides of the body.

9. An antenna assembly by which a medical device that is implanted in a patient receives a radio frequency signal, wherein the radio frequency signal has at least a first B field, a second B field and a third B field each oriented in a different direction, said antenna assembly comprising:
    a body having a cylindrical surface;
    a first antenna oriented at the medical device so as to receive the first B field, and located on the cylindrical surface;
    a second antenna oriented at the medical device so as to receive the second B field, and located on the cylindrical surface and spaced 90° circumferentially from the first antenna; and
    a third antenna oriented at the medical device so as to receive the third B field.

10. The antenna assembly as recited in claim 9 wherein:
    the first antenna comprises a first conductive coil and a second conductive coil that is connected to and spaced from the first conductive coil along a first axis; and
    the second antenna comprises a third conductive coil and a fourth conductive coil that is connected to and spaced from the third conductive coil along a second axis that is transverse to the first axis.

11. The antenna assembly as recited in claim 10 wherein the first axis is substantially orthogonal to the second axis.

12. The antenna assembly as recited in claim 10 wherein the third antenna comprises a fifth conductive coil wound about along a third axis that is transverse to the first axis and the second axis.

13. The antenna assembly as recited in claim 9 further comprising a passive network connected to the first antenna, the second antenna, and the third antenna and combining electrical signals produced in those antennas.

14. The antenna assembly as recited in claim 9 wherein the body is tubular.

15. The antenna assembly as recited in claim 9 wherein the third antenna is wound circumferentially around the body.

16. An antenna assembly by which a medical device implanted in a patient receives a radio frequency signal, wherein the medical device has a body with a cylindrical surface, said antenna assembly comprising:
    a first antenna located on the cylindrical surface to receive the radio frequency signal; and
    a second antenna located on the cylindrical surface and spaced 90° circumferentially from the first antenna.

17. The antenna assembly as recited in claim 16 wherein the first antenna and the second antenna each comprises a conductive coil wherein the conductive coil of the first antenna is orthogonal to the conductive coil of the second antenna.

18. The antenna assembly as recited in claim 16 further comprising a third antenna having another conductive coil wound circumferentially around the body.

19. The antenna assembly as recited in claim 16 wherein:
    the first antenna comprises a first conductive coil and a second conductive coil that is connected to and spaced from the first conductive coil along a first direction; and
    the second antenna comprises a third conductive coil and a fourth conductive coil that is connected to and spaced from the third conductive coil along a second direction that is orthogonal to the first direction.

20. The antenna assembly as recited in claim 19 further comprising a third antenna having a fifth conductive coil wound circumferentially around the body.

* * * * *